United States Patent
Ono et al.

(10) Patent No.: US 8,359,118 B2
(45) Date of Patent: Jan. 22, 2013

(54) METHOD OF PRODUCING FLEXIBLE VESSEL MODEL FOR SIMULATING SURGICAL OPERATION

(75) Inventors: Hidenori Ono, Setagaya-ku (JP); Akio Morita, Shinagawa-ku (JP)

(73) Assignee: Ono & Co., Ltd., Tokyo (JP)

( * ) Notice: Subject to any disclaimer, the term of this patent is extended or adjusted under 35 U.S.C. 154(b) by 246 days.

(21) Appl. No.: 12/991,115

(22) PCT Filed: May 7, 2009

(86) PCT No.: PCT/JP2009/058964
§ 371 (c)(1),
(2), (4) Date: Nov. 4, 2010

(87) PCT Pub. No.: WO2009/139431
PCT Pub. Date: Nov. 19, 2009

(65) Prior Publication Data
US 2011/0060446 A1    Mar. 10, 2011

(30) Foreign Application Priority Data

May 12, 2008    (JP) ................................. 2008-125008

(51) Int. Cl.
*G06F 19/00* (2006.01)
*G09B 23/28* (2006.01)
*A61B 17/08* (2006.01)
*A61B 17/22* (2006.01)
*A61D 1/02* (2006.01)

(52) U.S. Cl. ......... 700/119; 434/272; 606/158; 606/159

(58) Field of Classification Search ................ 700/95, 700/117–119; 434/262, 267, 272, 275; 606/151, 606/155, 157–159
See application file for complete search history.

(56) References Cited

U.S. PATENT DOCUMENTS 6,932,610 B2    8/2005    Ono et al.
(Continued)

FOREIGN PATENT DOCUMENTS

EP    1 677 273 A1    7/2006
JP    2003-241647 A    8/2003
(Continued)

OTHER PUBLICATIONS

Supplementary European Search Report mailed on Oct. 18, 2012 for EP 09 74 6637.

*Primary Examiner* — Crystal J Barnes-Bullock
(74) *Attorney, Agent, or Firm* — Holtz Holtz Goodman & Chick PC

(57) ABSTRACT

A method of producing a flexible vessel model for simulating a surgical operation, which is a three-dimensional model being capable of reproducing an aneurysm or narrowing occurring in the artery or vein based on CT/MRI image data of a patient obtained in practice and thus allowing vascular therapy trainings and preoperative simulations, with the use of a precise lamination modeling machine, wherein a vascular model having an affected part is fabricated by using a lamination technique together with a supporting material for sustaining the shape of the three-dimensional model during the fabrication in the precise lamination modeling machine and, after the completion of the fabrication by the lamination machine technique, the supporting material is removed. Thus, it is possible to provide a three-dimensional vascular model whereby the shape of an aneurysm or narrowing occurring in the artery or vein, which is to be used in preoperative simulation of vascular therapy for the artery or vein, can be reproduced with the use of a flexible polymer model and thus vascular therapy trainings and preoperative simulation can be carried out by using the same.

3 Claims, 1 Drawing Sheet

U.S. PATENT DOCUMENTS

| | | | |
|---|---|---|---|
| 7,371,067 B2* | 5/2008 | Anderson et al. | 434/262 |
| 7,583,367 B2* | 9/2009 | Ikeda et al. | 356/32 |
| 7,625,211 B2* | 12/2009 | Feygin et al. | 434/275 |
| 8,048,150 B2* | 11/2011 | Weber et al. | 623/1.42 |
| 2005/0181343 A1* | 8/2005 | Ault et al. | 434/272 |
| 2005/0186361 A1* | 8/2005 | Fukuda et al. | 428/15 |
| 2009/0024152 A1* | 1/2009 | Boyden et al. | 606/155 |

FOREIGN PATENT DOCUMENTS

| | | |
|---|---|---|
| JP | 2004-184606 A | 7/2004 |
| JP | 2006-201291 A | 8/2006 |
| JP | 2008-070847 A | 3/2008 |
| WO | 2006/083963 A2 | 8/2006 |

\* cited by examiner

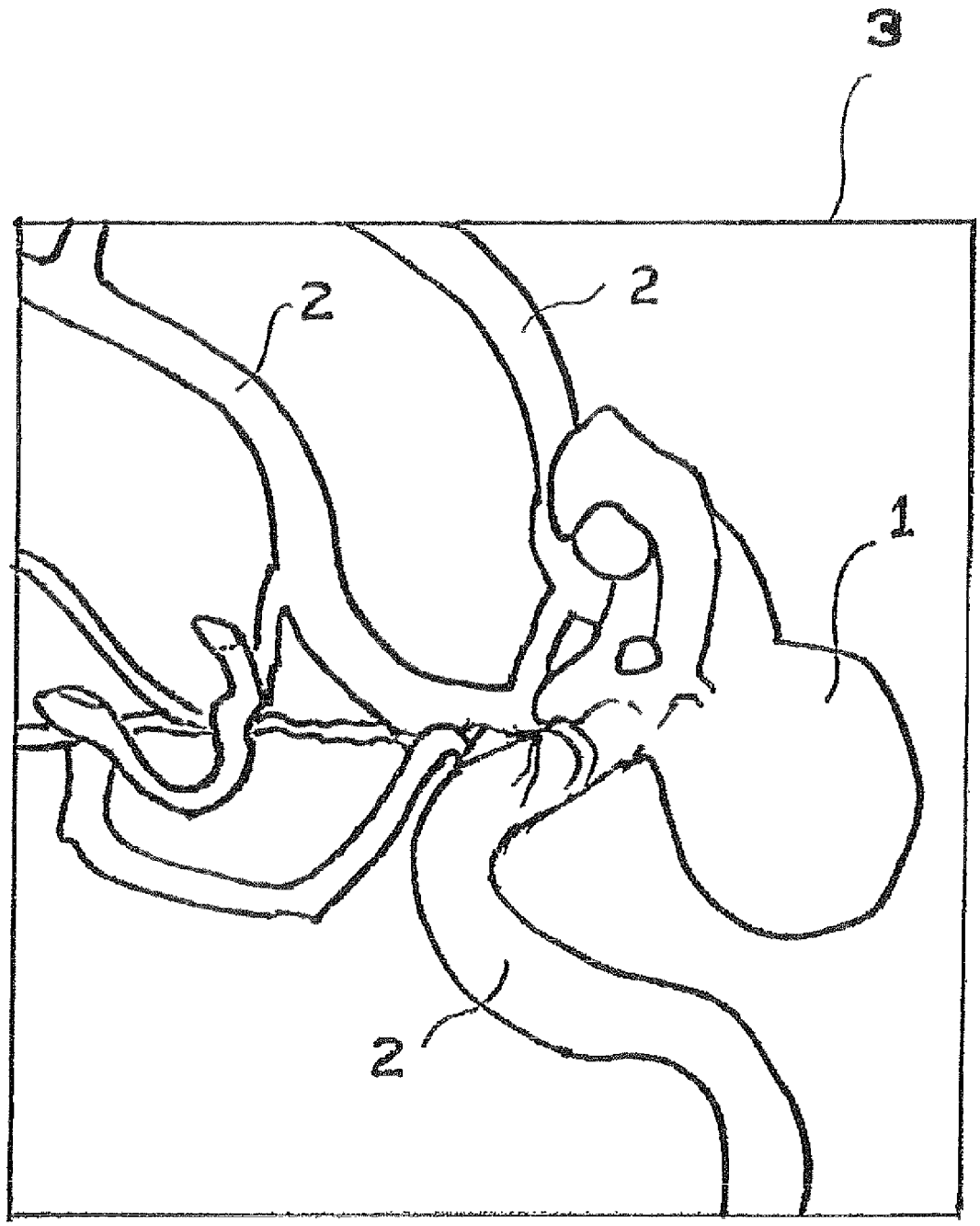

METHOD OF PRODUCING FLEXIBLE VESSEL MODEL FOR SIMULATING SURGICAL OPERATION

TECHNICAL FIELD

The present invention relates to a method of producing a flexible vessel model for simulating a surgical operation which enables to decide the method of the operation in advance by understanding steric and local relations of blood vessels in the domain close to the affected part before vascular therapy of an artery or a vein is conducted and to achieve the optimum treatment by predicting a change in shape of the blood vessels taking place as the result of the operation. More particularly, the present invention relates to a method of producing a flexible vessel model for simulating a surgical operation which is useful in the vascular therapy of aneurysm occurring in a brain artery using a clip, a coil or a stent.

BACKGROUND ART

In the vascular therapy of an artery or a vein, treatments of an aneurysm and bypassing, abscission and anastomosis of a blood vessel are mainly conducted for arteries, and treatments of a varix, treatments using a catheter, shunt, exscission and ablation with laser or radio wave are conducted for veins.

With respect to the aneurysm among the therapies set forth above, no symptoms are found even when an aneurysm without rupture is present. However, when the aneurysm is ruptured, internal hemorrhage takes place, and this causes a serious result leading to danger on life, occasionally.

For example, in the case of a brain aneurysm, when an aneurysm having the possibility of rupture is found, therapies such as a therapy in which the flow of the blood stream into the aneurysm is stopped by clipping the base part of the aneurysm from the outside, and a therapy in which the flow of the blood stream into the aneurysm is prevented by placing a coil at the inside of the aneurysm or by placing various types of stents at the inside of a blood vessel at the base part of the aneurysm, have been widely conducted.

An aneurysm has a shape protruded at the outside of a blood vessel like a hill slope. For example, it is desirable from the standpoint of preventing rupture of the aneurysm that clipping is made at a position closer to the foot of the hill slope. However, when the position of the clipping is excessively close to the foot of the hill slope as the shape of the aneurysm, narrowing or strain tends to be formed in the vascular membrane in the vicinity of the position of the clipping, or change in the steric form tends to take place in the vicinity of the aneurysm due to bending. As the result, the form of the blood stream becomes unstable, and the smooth flow of the blood is adversely affected. Similarly, when a coil or a stent is used, the form of the blood stream becomes unstable after the operation depending on the size of the coil or the stent or the position where the coil or the stent is placed.

In the case of the operation on an un-ruptured aneurysm, even if it is confirmed that nothing abnormal is found on the shape and the flow of the blood stream in a condition that the portion of the operation is opened or in a condition that a catheter is inserted for the use of a clip, a coil or a stent, it is not possible to confirm during the operation the stability of the shape of the blood vessel after the operation since the tension on flexible thin blood vessels changes when the operation is completed after the portions opened during the operation are anastomosed and the catheter is removed. When an adverse effect on the smooth flow of the blood is found, the operation is conducted again, and the entire treatment on the aneurysm such as clipping must he conducted again.

In such a case, it would be a great merit for both of the patient and the operator, if it is possible to conduct a preoperative simulation to confirm that no adverse effects are found on the steric shape of the blood vessel which is formed after the operation which will result in obstruction of the blood stream by preparing a model of the shape of the blood vessel of the patient for the operation and testing the type, the number and the position of placement of the clip or the position and the method of placement of a coil or the like, since it enables to conduct the optimum treatment using a clip, a coil or a stent rapidly in the operation.

As the model for the preoperative simulation, the present inventor has proposed a method for producing a human bone model for simulation of the operation in accordance with the lamination modeling method in which the model is divided into thin layers and each thin layer is formed by sintering a powder material with laser (Patent Reference 1).

However, in accordance with the above method, a model of the human bone is formed with a material which has approximately the same hardness as that of the human bone and can be cut as easily as the human bone. A model of a flexible vascular shape such as a model of a blood vessel, which is the subject of the present invention, cannot be prepared in accordance with the above method.

When a vascular shape is formed in accordance with the method of preparing a hard model as described above, the model is suitable for understanding the steric relation of the positions of the affected part and the blood vessel and examining the direction of the operation, e.g., the direction of inserting a clip. However, the effect of the operation on the shape of the blood vessel after the operation has been completed cannot be confirmed. Moreover, the simulation cannot be conducted under the condition such that a coil or a stent is inserted at the inside.

No references which provide a model of a hollow tubular shape of a flexible portion for the operation such as a blood vessel can be found heretofore.

[Patent Reference 1] Japanese Patent No. 3927487

DISCLOSURE OF THE INVENTION

Problems to be Overcome by the Invention

The present invention has an object of providing a steric vessel model for preoperative simulation used in a treatment of blood vessel which reproduces, using a model made of a flexible polymer, the shape of an aneurysm or a narrowing occurring in an artery or a vein and allows training and the preoperative simulation in a treatment of blood vessel using instruments for operation such as clips, coils and stents by using the model.

Means for Overcoming the Problems

For lamination modeling of a flexible vessel model based on formation of thin layers in the present invention, it is necessary that the steric positions of a flexible vessel model are fixed during the preparation. A method was found in which a supporting material was laminated using a precise lamination modeling machine in combination with the flexible material for forming the vascular membrane model to fix the shape, and the supporting material was removed after the vessel model was produced, and the present invention has been completed based on the knowledge.

The present invention provides:

(1) A method of producing a flexible vessel model for simulating a surgical operation which comprises:

forming a steric shape of blood stream based on a image data of the blood stream in a target part of a predesignated artery or vein in contrast enhanced Computer Tomogram;

obtaining a data on a steric shape of a vascular membrane by adding a thickness of the vascular membrane to a surface shape of the steric shape of blood stream;

cutting out data on the steric shape of a vascular membrane in the target part from the data on a steric shape of the vascular membrane obtained above with a space domain in a manner such that the space domain contains the target part having a prescribed size;

preparing a three-dimensional data of the vascular membrane in a manner such that the steric shape of the vascular membrane in the target part is suspended in the space domain;

inputting the three-dimensional data into a computer of a precise lamination modeling machine equipped with jet nozzles capable of jetting a flexible polymer in a form of minute liquid droplets having a diameter of 50 μm or smaller and jet nozzles capable of jetting a supporting material in a form of minute liquid droplets having a diameter of 50 μm or smaller;

outputting a data of a planar thin layer comprising a vascular membrane portion area and a space portion area obtained by cutting the three-dimensional data with planes parallel with a bottom face of the three-dimensional data into a prescribed thin unit layer having a thickness of 0.1 mm or smaller based on the three-dimensional data input into the computer;

forming a vascular membrane portion having a thickness of the thin unit layer by jetting the flexible polymer by outputting the data of the vascular membrane portion area of the data of the planar thin layer and simultaneously forming a supporting material layer by outputting a jet nozzle jetting signal to jet the droplets of the supporting material in the data of the space portion area, and thereby conducting a procedure to form a vascular vessel model surrounded by the supporting material in the thin unit layer of the three-dimensional data having a thickness of 0.1 mm or smaller, and repeating above procedure successively for each of the planar thin unit layers from a bottom layer to an uppermost layer in the three-dimensional data to obtain a block matrix in which the flexible vessel model formed with the flexible polymer and having a steric shape of the vascular membrane is suspended at an inside of a matrix of the supporting material having an outside shape corresponding to the three-dimensional data;

removing the supporting material attached to the outside of the flexible vessel model, and taking out the flexible vessel model embedded at an inside of the block matrix from the block matrix; and removing the supporting material present at an inside of the taken out flexible vessel model through openings of the vessel model;

(2) The method of producing a flexible vessel model for simulating a surgical operation according to (1), wherein the target part is a part of a blood vessel where an aneurysm is present; and (3) The method of producing a flexible vessel model for simulating a surgical operation according to (1), wherein the target part is a part of a blood vessel where a varix is present.

The Effect of the Invention

The flexible vessel model produced in accordance with the present invention is useful in the treatment of blood vessels for artery or vein, particularly in decreasing the time for operation of an un-ruptured aneurysm and in preventing medical accidents since it enables to conduct the treatment predesignated for the blood vessel in practice and to confirm the presence or the absence of change in shape, wrinkles and strains occurring on the vascular membrane and the shape of the vascular membrane, and thereby to study the optimum treatment.

Furthermore, the method of the present invention using a support material exhibits an advantage in that the steric shape of a flexible blood vessel can be accurately modeled.

BRIEF DESCRIPTION OF THE DRAWINGS

FIG. 1 shows an oblique sectional view exhibiting the vessel model for medical use produced in the Example of the present invention. In the Figure, reference numerals mean as follows: 1: a part corresponding to an aneurysm; 2: a part corresponding to a blood vessel in the vicinity of an aneurysm; and 3: a boundary of a three-dimensional image.

THE MOST PREFERRED EMBODIMENT TO CARRY OUT THE INVENTION

In the method of the present invention, as the first step, a contrast medium is jetted, and an image data of blood stream in a target part of a predesignated artery or vein in contrast enhanced computer tomogram is obtained.

From the image data of blood stream in the target part of the predesignated artery or vein in contrast enhanced computer tomogram, the steric shape of blood stream is extracted. The thickness of the vascular membrane is added to the surface shape of the steric shape of blood stream extracted above, and data on the steric shape of the vascular membrane having the thickness is obtained. It is possible to input the average thickness of the vascular membrane in the target part as the thickness of the vascular membrane.

The data on the steric shape of the vascular membrane in the target part is cut out with a space domain from the data on the steric shape of the vascular membrane obtained above in a manner such that the space domain contains the target part having a prescribed size and a three-dimensional data is prepared in a manner such that the steric shape of the vascular membrane in the target part is suspended in the space domain. The position of the flexible blood vessel during the production can be stabilized by forming the bottom face in the space domain.

In the production of the flexible vessel model of the present invention, it is possible to use a precise lamination modeling machine which forms each thin layer of a laminate with a material and fixes each of the layers in a laminate in accordance with the inkjet process. This is an apparatus which laminates many sectional layers of a vascular membrane to form a steric shape of the vascular membrane by the lamination like a printing process in which many thin printing layers are repeatedly printed. However, even if a complicated steric shape of a vascular membrane is formed by the lamination, a successive printing for laminating the next layer cannot proceed unless the shape formed previously is fixed. Therefore, it is necessary that a supporting material is disposed in the space domain to fix the position of the vascular membrane.

In the production of the flexible vessel model of the present invention, a lamination layer of a thin unit layer in the three-dimensional data is partitioned in a manner such that a long and narrow area of a section of the vascular membrane having a small thickness is surrounded by a space area having a large area. A flexible polymer is jetted into the area of the vascular membrane in accordance with the inkjet process to form a thin unit layer of the vascular membrane and the laminate of a thin unit layer in which a long and narrow area of a section of the vascular membrane having a small thickness is surrounded by a large area of the supporting material which is simultaneously formed with an overlay print layer of solid printing process using the supporting material as the ink in accordance with the inkjet process. When the lamination of the thin unit layer is completed for the entire three-dimensional data, a block of the supporting material in which the steric shape of the vascular membrane of the target part is suspended can be obtained. When the supporting material is removed from the block by peeling off the supporting material or by dissolving the supporting material with a solvent such as water, the steric model of the vascular membrane still containing the supporting material at the inside appears while the steric shape is sustained. When the supporting material remaining at the inside is taken out from openings of the model of the vascular membrane and removed, the vessel model of the object product can be obtained.

As the inkjet type lamination modeling machine used in the present invention, for example, the lamination modeling machine "EDEN 500V" manufactured by Object Geometries Ltd., which is commercially available, can be used.

This apparatus is an inkjet type lamination modeling machine forming thin unit layers and is an apparatus similar to the two-color printing machine in printing.

For each thin unit layer of lamination in the three-dimensional data, the entire area of the thin unit layer is divided into the area of a section of the vascular membrane and the space area. To form each thin unit layer of lamination, a material for the vessel model comprising a flexible polymer for forming the portion corresponding to the section of the vascular membrane is jetted to the area of a section of the vascular membrane for lamination and a supporting material for sustaining the shape is jetted to the space area. A thin unit layer for lamination is formed in this manner. The thin unit layers are successively laminated, and a steric model of the vascular membrane made of the flexible polymer and a domain of the space comprising the supporting material are formed.

The three-dimensional data showing the steric shape of the vascular membrane of the target part suspended in the space domain having the bottom face described above is input into a computer of a precise lamination modeling machine equipped with jet nozzles capable of jetting a flexible polymer in a form of minute liquid droplets having a diameter of 50 μm or smaller and jet nozzles capable of jetting a supporting material in a form of minute liquid droplets having a diameter of 50 μm or smaller. Based on the three-dimensional data input into the computer, each of the thin planer data comprising an area of the vascular membrane and a space area which is obtained by cutting the three-dimensional data with planes parallel with the bottom face of the three-dimensional data into thin layers each having a prescribed thickness of 0.1 mm or smaller is output and the output data of the vascular membrane area of the thin planer data is output as the jetting signal for jetting the liquid droplets of the flexible polymer, and a portion corresponding to the vascular membrane having a thickness of the planar thin unit layer is formed by jetting of the flexible polymer. Simultaneously, output data of the space area of the thin planer data is output as the jetting signal for jetting the liquid droplets of the supporting material, and a supporting material layer having a thickness of the planar thin unit layer is formed by jetting of the supporting material. The thin layer formed in the above procedure is adhered tightly to the part corresponding to the vascular membrane and the supporting part in the layer laminated previously to form integrally adhered layers, and a laminate corresponding to one layer is added to the portion laminated previously. The thickness of one layer in the lamination can be suitably decided based on the accuracy of the lamination modeling machine, the accuracy required for the shape of the vessel model and the productivity of production of the model. The thickness is, in general, 0.1 mm or smaller, preferably 0.1 mm to 0.005 mm and more preferably 0.05 to 0.01 mm. The thickness decides the pitch of jetting in the direction of height in the production of the vessel model. When the thickness is smaller, the sectional shape in the vertical direction of the vessel model is more accurate, and the condition of strain in the shape after the treatment with a clip or the like can be reproduced more precisely.

By repeating the operation of lamination comprising forming the area of the vascular membrane model and the support area of the space area which tightly contacts the area of the vascular membrane model in the thin unit layer having a thickness of 0.1 mm or smaller in the domain of the three-dimensional data successively on each planar thin unit layer from a bottom layer to an uppermost layer of the domain of the three-dimensional data, a block matrix in which the flexible vessel model formed with the flexible polymer having the steric shape of the vascular membrane is suspended at the inside of a matrix of the supporting material having an outer shape corresponding to the three-dimensional data can be obtained. By removing the supporting material attached to the outside of the flexible vessel model by peeling off or by dissolving the supporting material the flexible vessel model at the inside of which the supporting material is filled which has been embedded at the inside of the block matrix from the block matrix can be taken out. The supporting material present at the inside of the taken out flexible vessel model can be removed by scraping out the supporting material or by dissolving the supporting material through openings of the vessel model. Thus, a hollow vascular membrane model having the same steric shape as that of the vascular membrane in practice can be obtained.

When the flexible vessel model is a model of a blood vessel having an aneurysm, the aneurysm can be clipped with one or more clips or can be clipped at various positions, and the optimum method of clipping in relation to the condition of strain formed depending on the method of clipping can be confirmed before the actual operation. When placement of a coil or a stent is selected as the optimum method in accordance with the shape of portion of the blood vessel having the aneurysm, coils and stents having various sizes can be placed into the vessel model, and the shape of the blood vessel causing no abnormal flow of blood after the insertion can be confirmed before the operation.

The ink substance jetted from the inkjet nozzle which jets the material of the flexible vessel model of the present invention is not particularly limited as long as the ink substance is a flexible rubbery polymer substance, exhibits the property of forming a thin film, can be jetted from an inkjet nozzle as minute liquid droplets, is immediately solidified after being jetted to form a layer of a laminate, and integrally attached to the rubbery polymer substance which has been laminated as the lower layer to form the model of a vascular membrane.

As the ink substance of the material of the flexible vessel model, an ink substance which is a liquid prepolymer of a rubbery polymer and comprises a photocurable liquid prepolymer substance containing no solvents is preferable. This ink substance is supplied to a cartridge connected to the inkjet nozzle, formed into minute particles by the jetting and jetted to the area of the vascular membrane. In the minute particles jetted from the inkjet nozzle, the polymerization proceeds with ultraviolet light while the particles fly under irradiation with ultraviolet light. The ink substance is converted into a flexible polymer and attached to the area of the vascular membrane.

As the ink substance, for example, "FullCure 930 TangoPlus" manufactured by Object Geometries Ltd. can be used.

"FullCure 930 TangoPlus" is a liquid composition comprising exo-1,7,7-trimethylbicyclo[2.2.1]hept-2-yl acrylate), a urethane acrylate oligomer, a small amount of a urethane resin and a photopolymerization initiator.

The ink substance is jetted from the tip of the inkjet nozzle as minute liquid droplets. When the ink substance is attached to the area of the vascular membrane, the attached ink substance forms an integral mixture with droplets already attached by previous printings and simultaneously, polymerization takes place due to the photopolymerization initiator dissolved in the ink substance with ultraviolet light applied during the jetting, and the prepolymer is converted into a flexible polymer instantaneously to obtain the flexible polymer substance forming the flexible vessel model.

As the ink substance jetted from the inkjet nozzle which jets the substance of the supporting material of the present invention, it is sufficient that the ink substance is a substance which is jetted from the inkjet nozzle as minute liquid droplets and is solidified immediately after being jetted to form a laminate layer. Any material can be used without restrictions as long as the material can be easily peeled off from the interface with the material forming the vessel model or easily separated from or dissolved and removed from the flexible polymer of the material forming the vessel model with water or a solvent such as an alcohol. For example, a substance which is converted into a flexible solid substance exhibiting the ability of sustaining the shape necessary for sustaining the shape during the production of a product having a small weight such as the vascular membrane model and can be easily pulverized by application of force, is particularly preferable. Since the above substance is a flexible solid substance, the possibility that the vascular membrane model made of the flexible polymer is damaged while the supporting material is removed, is small. Examples of the ink substance forming the supporting material include "FullCure 705" manufactured by Object Geometries Ltd..

In the present invention, the ink of the flexible rubbery substance and the ink of the substance of the supporting material are packed into liquid storage tanks (cartridges) of the inkjet nozzles which jet the material of the flexible vessel model and the inkjet nozzles which jet the substance of the supporting material in the precise lamination modeling machine, and the inks are jetted in an amount such that a layer having the thickness of a single layer of a laminate described above is formed. As the area of the jetting, the jetting is made in the area of the vascular membrane and the space area in each thin unit layer in the three-dimensional data, thus forming the lamination of each thin unit layer is conducted.

The accuracy of the pattern formed by the jetting separately for each of the vascular area and the space area is decided by the distance between pitches of the jetting. In the precise lamination modeling machine used in the present invention, the pitch in the horizontal X, Y directions can be adjusted, in general, to 0.1 mm or smaller, preferably from 0.1 mm to 0.005 mm and more preferably 0.05 mm to 0.01 mm similarly to the pitch of jetting in the vertical direction as set forth above.

The jetted flexible polymer is in the form of minute liquid droplets having a diameter of 50 μm or smaller. When the diameter exceeds 50 μm, the shape of the vascular membrane becomes inaccurate.

EXAMPLES

A vessel model having an un-ruptured aneurysm made of a flexible polymer was prepared using a precise lamination modeling machine manufactured by Object Geometries Ltd. "EDEN 500V" (the size of modeling: 490 mm×390 mm×200 mm; the size of the machine: 1320 mm×990 mm×1200 mm; the pitch of lamination: 0.016~0.030 mm). The precise lamination modeling machine manufactured by Object Geometries Ltd. "EDEN 500V" is equipped with eight inkjet nozzles which can each jet two types of ink, and each inkjet nozzle is equipped with 96 holes for jetting minute liquid droplets at the tip. The eight inkjet nozzles having many holes for jetting minute liquid droplets provides the function of printing and lamination by rapidly jetting the ink uniformly over the unit area of lamination.

The two types of the ink are supplied to each of the eight inkjet nozzles from a cartridge of the first ink and a cartridge of the second ink.

In the present examples, the pitch of lamination in the vertical direction was set at 0.03 mm, and the lamination modeling was conducted at a pitch of jetting in the horizontal directions (the X- and Y-directions) of 0.05 mm. When the pitch was 0.1 mm or greater, the accurate reproduction of the operation of the accurate vascular membrane becomes difficult. The pitch of lamination in the vertical direction set at 0.03 mm was the same as the thickness of the single thin film.

As the ink substance used as the material of the flexible vessel model in the lamination modeling machine manufactured by Object Geometries Ltd., an ink, "FullCure 930 TangoPlus" manufactured by Object Geometries Ltd., containing a photo-polymerization initiator was selected and packed into the cartridge of the first ink. The physical properties of the polymer obtained by photopolymerization of the ink, i.e., the physical properties of the material of the vessel model, were as follows: the tensile strength at break: 1,455 MPa; the 20% modulus: 0.146 MPa; the 50% modulus: 0.263 MPa; the elongation: 218%; the Shore hardness: 27; the resistance to tensile force: 3.47 kg/cm; the glass transition temperature: −9.6° C.

As the ink for the supporting material, an ink "FullCure 705" made of a water soluble polyethylene glycol which can be easily pulverized was selected among inks of flexible resins for the supporting material specific for the lamination modeling machine manufactured by Object Geometries Ltd. and packed into the cartridge of the second ink.

A Computer Tomogram Image of a domain of a vascular area having an un-ruptured aneurysm of a patient appointed by the doctor in charge was obtained by 3DCTA using a contrast medium, and an three-dimensional data of the steric shape of the blood stream was obtained. (It is possible to obtain three-dimensional data of the steric shape of the blood stream from the picture of MRI of blood stream containing a contrast medium in place of the Computer Tomogram Image.)

A vascular membrane having a thickness of 0.3 mm was added to the surface of the three-dimensional data of the steric shape of the blood stream by the data processing, and data of the three-dimensional shape of the steric vessel model were obtained.

A computer was arranged so that the data of the three-dimensional shape of the steric vascular membrane obtained above could be output as data of unit layers having a thickness of 0.03 mm.

The lamination modeling machine manufactured by Object Geometries Ltd. has a space of 490 mm×390 mm×200 mm as the space for modeling.

Ten sets of three-dimensional data of the domain for modeling to be worked in the lamination having the size of 35 mm×30 mm×28 mm were copied from the data for laminating layers prepared above, and ten sets of the data of the unit layers for lamination were input in the above precise lamination modeling machine.

Data for each unit layer for lamination were output from the format for lamination modeling in the lamination modeling machine, and the ink corresponding to each area was jetted into the area of the vascular membrane and the space area (the area of the supporting material). This procedure was repeated, and a vascular membrane having the steric shape surrounded with the supporting material was prepared in 2 hours.

Ten blocks of the supporting material having the size of modeling of 35 mm×30 mm×28 mm containing the steric vascular membrane in the domain of the object of the operation were formed in the space for modeling in the laminating modeling machine in a manner such that the ten blocks are separated from one another as islands. The supporting material was peeled off with fingers from the surface of the ten blocks, and the vessel models having the steric shape shown in FIG. 1 were taken out. Since the inside of the models was filled with the water-soluble flexible solid supporting material and the flexible supporting material sustains the shape of the blood vessel, the vessel model containing the supporting material at the inside which had been taken out sustained the same shape as that of the affected part having the actual aneurysm. The steric positional relations between the blood vessel in the domain close to the affected part which are going to be operated and the aneurysm could be understood by observing the obtained model.

Then, the supporting material at the inside was taken out from the openings with sufficient care so that the vascular membrane was not damaged.

For this procedure, the part of the vessel model in the vicinity of the opening was rubbed, and the supporting material in the part in the vicinity of the opening was taken out. This procedure was repeated for adjacent parts of the vessel model successively, and the supporting material in the vessel model could be taken out. As the final procedure, the inside of the vessel model was washed with water, and the supporting material soluble in water at the inside of the vessel model was completely removed.

Using the obtained vessel model having the aneurysm, various types of clips to be used and coils and stents to be placed at the inside were placed at various positions of the aneurysm, and strains formed on the vascular membrane in the vicinity of the aneurysm was studied. The optimum type and number of the clip, the optimum position of the clip, and the optimum size and shape of the coil and the stent could be selected.

Industrial Applicability

Using the vessel model for medical application of the present invention, the condition of the blood vessel after the operation can be confirmed in advance to the actual operation of arteries or veins. Therefore, the present invention exhibits the advantage of achieving accurate and rapid operation of arteries and veins and can be widely applied to the industry of medical instruments used for the vascular therapy using clips, stents and coils.

The invention claimed is:

1. A method of producing a flexible vessel model for simulating a surgical operation which comprises:

forming a steric shape of blood stream based on a image data of the blood stream in a target part of a predesignated artery or vein in contrast enhanced computer tomogram;

obtaining data on a steric shape of a vascular membrane by adding thickness of the vascular membrane to a surface shape of the steric shape of blood stream;

cutting out data on the steric shape of a vascular membrane in the target part from the data on a steric shape of the vascular membrane obtained above with a space domain in a manner such that the space domain contains the target part having a prescribed size;

preparing a three-dimensional data of the vascular membrane in a manner such that the steric shape of the vascular membrane in the target part is suspended in the space domain;

inputting the three-dimensional data into a computer of a precise lamination modeling machine equipped with jet nozzles capable of jetting a flexible polymer in a form of minute liquid droplets having a diameter of 50 μm or smaller and jet nozzles capable of jetting a supporting material in a form of minute liquid droplets having a diameter of 50 μm or smaller;

outputting a data of a planar thin layer comprising a vascular membrane portion area and a space portion area obtained by cutting the three-dimensional data with planes parallel with a bottom face of the three-dimensional data into a prescribed thin unit layer having a thickness of 0.1 mm or smaller based on the three-dimensional data input into the computer;

forming the vascular membrane portion area having a thickness of the thin unit layer by jetting droplets of the flexible polymer by outputting the data of the vascular membrane portion area and simultaneously forming the supporting material layer by outputting the data of the space portion area as a jet nozzle signal to jet the droplets of the supporting material, and thereby conducting a procedure to form a vascular vessel model surrounded by the supporting material in the thin unit layer of the three-dimensional data having a thickness of 0.1 mm or smaller, and repeating above procedure successively for each of the planar thin unit layers from a bottom layer to an uppermost layer in the three-dimensional data to obtain a block matrix in which the flexible vessel model formed with the flexible polymer and having a steric shape of the vascular membrane is suspended at an inside of a matrix of the supporting material having an outside shape corresponding to the three-dimensional data;

removing the supporting material attached to the outside of the flexible vessel model, and taking out the flexible vessel model embedded at an inside of the block matrix from the block matrix; and removing the supporting material present at an inside of the taken out flexible vessel model through openings of the vessel model.

2. The method of producing a flexible vessel model for simulating a surgical operation according to claim 1, wherein the target part is a part of a blood vessel where an aneurysm is present.

3. The method of producing a flexible vessel model for simulating a surgical operation according to claim 1, wherein the target part is a part of a blood vessel where a varix is present.

* * * * *